United States Patent [19]
Slassi et al.

[11] Patent Number: 5,998,462
[45] Date of Patent: *Dec. 7, 1999

[54] 5-ALKYL INDOLE COMPOUNDS

[75] Inventors: Abdelmalik Slassi; Louise Edwards, both of Mississauga; Qingchang Meng, Georgetown; Sumanas Rakhit, Mississauga, all of Canada

[73] Assignee: Allelix Biopharmaceuticals Inc., Ontario, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/767,323

[22] Filed: Dec. 16, 1996

[51] Int. Cl.$^6$ .................... A61K 31/40; C07D 403/06
[52] U.S. Cl. ............................. 514/414; 548/468
[58] Field of Search ............... 548/468; 514/414

[56] References Cited

U.S. PATENT DOCUMENTS

| | | | |
|---|---|---|---|
| 4,870,085 | 9/1989 | Glaser et al. | 514/323 |
| 5,348,968 | 9/1994 | Lavielle et al. | 514/360 |
| 5,496,957 | 3/1996 | Glennon | 548/491 |
| 5,504,101 | 4/1996 | Glennon | 514/415 |

FOREIGN PATENT DOCUMENTS

| | | |
|---|---|---|
| 0 610 134 A1 | 8/1994 | European Pat. Off. . |
| JP 02037351B | 8/1990 | Japan . |
| WO 9424127 | 10/1994 | WIPO . |
| WO 9617842 | 6/1996 | WIPO . |

OTHER PUBLICATIONS

Glen, et al. Journal of Medicinal Chemistry, 1995, 38:3566–3580. "Computer–Aided Design and Synthesis of 5–Substituted Tryptamines and Their Pharmacology at the 5–HT1D Receptor: Discovery of Compounds with Potential Anti–Migraine Properties".

Chemical Abstracts, vol. 97, No. 17, Oct., 1982, abs. No. 144720k, Banglun et al. "Synthesis of N,N–disubstituted beta–hydroxy–tryptamines."

Macor, John, A direct synthesis of 3–(pyrrolidin–3–yl)indoles for Use as Conformationally Restricted Analogs of Tryptamines (Apr., 1997), pp. 443–449, Synthesis.

*Primary Examiner*—Patricia L. Morris
*Attorney, Agent, or Firm*—Nikaido Marmelstein Murray & Oram, LLP

[57] ABSTRACT

Described herein are compounds selective for the 5-HT$_{1D}$-like receptor, which have the general formula:

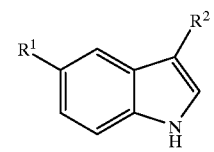

I wherein:

R$^1$ is linear or branched loweralkyl;
R$^2$ is selected from a group of Formula II, III, IV and V:

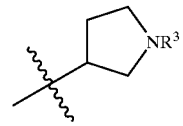

II

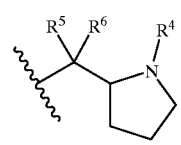

III

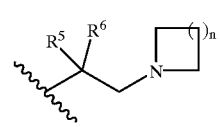

IV

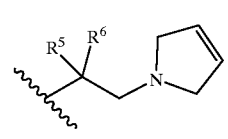

V

R$^3$ is selected from H and loweralkyl;
R$^4$ is selected from H and loweralkyl;
One of R$^5$ and R$^6$ is H and the other is independently selected from H, loweralkoxy, loweralkyl and hydroxy; and
n is 1–3;
or a salt, solvate or hydrate thereof.

Also described is the use of these compounds as pharmaceuticals to treat indications where stimulation of the 5-HT$_{1D}$-like receptor is implicated, such as migraine.

7 Claims, No Drawings

5-ALKYL INDOLE COMPOUNDS

This invention relates to 5-alkyl-substituted indole compounds, to pharmaceutical compositions containing them and to their medical use, particularly in the treatment of CNS conditions.

According to one aspect of the invention, there are provided compounds of Formula I and salts, solvates or hydrates thereof:

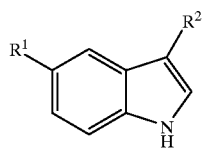

I wherein:
$R^1$ is linear or branched loweralkyl;
$R^2$ is selected from a group of Formula II, III, IV and V:

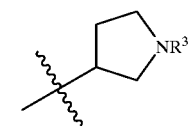

II

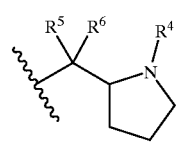

III

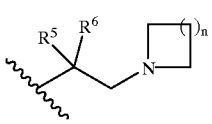

IV

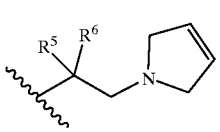

V $R^3$ is selected from H and loweralkyl;
$R^4$ is selected from H and loweralkyl;
One of $R^5$ and $R^6$ is H and the other is independently selected from H, loweralkoxy, loweralkyl and hydroxy; and
n is 1–3.

According to another aspect of the invention, there is provided a pharmaceutical composition comprising a compound of Formula I in an amount effective to stimulate 5-$HT_{1D}$-like receptors, and a pharmaceutically acceptable carrier.

In another aspect of the present invention there are provided compositions containing the present compounds in amounts for pharmaceutical use to treat CNS conditions where a 5-$HT_{1D}$-like ligand is indicated. These and other aspects of the present invention are described in greater detail hereinbelow.

DETAILED DESCRIPTION AND PREFERRED EMBODIMENTS

The term "loweralkyl" as used herein means straight and branched chain alkyl radicals containing from one to six carbon atoms and includes methyl, ethyl, propyl, isopropyl, tert-butyl and the like.

The term "loweralkoxy" as used herein means straight and branched chain alkoxy radicals containing from one to four carbon atoms and includes methoxy, ethoxy, tert-butoxy and the like.

Compounds of Formula I include those in which, $R^1$ is loweralkyl. In preferred embodiments, $R^1$ is selected from methyl, ethyl, isopropyl, sec-butyl and t-butyl. In more preferred embodiments $R^1$ is selected from t-butyl and isopropyl.

In another embodiment of the invention, $R^2$ is selected from a group of Formula II, III, IV and V:

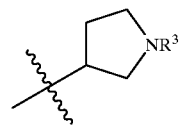

II

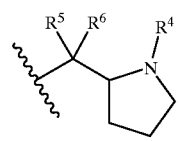

III

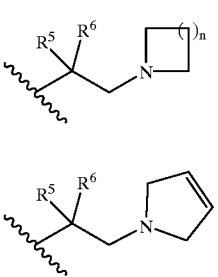

IV

V

In preferred embodiments, $R^2$ is selected from a group of Formula IV and V. In a more preferred embodiment, $R^2$ is a group of Formula IV.

When $R^2$ is a group of Formula II, $R^3$ is selected from H and loweralkyl. Preferably $R^2$ is loweralkyl, specifically, methyl. When $R^2$ is a group of Formula III, $R^4$ is selected from H and loweralkyl. In preferred embodiments, $R^4$ is loweralkyl, specifically, methyl. When $R^2$ is a group of Formula IV, one of $R^5$ and $R^6$ is H and the other is independently selected from H, loweralkoxy, loweralkyl and hydroxy and n is 1–3. Preferably $R^5$ and $R^6$ are both H and n is 2. When $R^2$ is a group of Formula V, one of $R^5$ and $R^6$ is H and the other is independently selected from H, loweralkoxy and hydroxy; preferably $R^5$ and $R^6$ are both H.

In specific embodiments of the invention, the compounds of Formula I include:
5-Isopropyl-3-(2-pyrrolidinylethyl)-1H-indole;
5-Tert-butyl-3-(2-pyrrolidinylethyl)-1H-indole;
5-Methyl-3-(2-pyrrolidinylethyl )-1H-indole;
5-Sec-butyl-3-(2-pyrrolidinylethyl)-1H-indole;
5-Sec-butyl-3-(2-pyrrolinylethyl)-1H-indole;
5-Methyl-3-(2-pyrrolinylethyl)-1H-indole;
(R)-5-Ethyl-3-[(N-methylpyrrolidin-2-yl)methyl]-1H-indole;
(R)-5-Methyl-3-[(N-methylpyrrolidin-2-yl)methyl]-1H-indole;
(R)-5-Methyl-3-[(pyrrolidin-2-yl)methyl]-1H-indole;
(S)-5-Methyl-3-[(N-methylpyrrolidin-2-yl)methyl]-1H-indole;

5-Ethyl-3-(N-methylpyrrolidin-3-yl)-1H-indole;
5-Methyl-3-(N-methylpyrrolidin-3-yl)-1H-indole;
(R)-5-Tert-butyl-3-[(N-methylpyrrolidin-2-yl)methyl]-1H-indole;
(R)-5-Isopropyl-3-[(N-methylpyrrolidin-2-yl)methyl]-1H-indole; and
5-Ethyl-3-(2-pyrrolidinylethyl)-1H-indole.

In preferred embodiments of the invention, the compounds of Formula I include:
5-Isopropyl-3-(2-pyrrolidinylethyl)-1H-indole;
5-Tert-butyl-3-(2-pyrrolidinylethyl)-1H-indole;
5-Methyl-3-(2-pyrrolidinylethyl)-1H-indole;
5-Methyl-3-(2-pyrrolinylethyl)-1H-indole;
5-Sec-butyl-3-(2-pyrrolidinylethyl)-1H-indole;
5-Sec-butyl-3-(2-pyrrolinylethyl)-1H-indole;
(R)-5-Ethyl-3-[(N-methylpyrrolidin-2-yl)methyl]-1H-indole;
(R)-5-Methyl-3-[(N-methylpyrrolidin-2-yl)methyl]-1H-indole;
(R)-5-Methyl-3-[(pyrrolidin-2-yl)methyl]-1H-indole;
(R)-5-Tert-butyl-3-[(N-methylpyrrolidin-2-yl)methyl]-1H-indole;
(R)-5-Isopropyl-3-[(N-methylpyrrolidin-2-yl)methyl]-1H-indole; and
5-Ethyl-3-(2-pyrrolidinylethyl)-1H-indole.

In more preferred embodiments of the invention, the compounds of Formula I include:
5-Isopropyl-3-(2-pyrrolidinylethyl)-1H-indole;
5-Tert-butyl-3-(2-pyrrolidinylethyl)-1H-indole;
5-Methyl-3-(2-pyrrolinylethyl)-1H-indole;
(R)-5-Ethyl-3-[(N-methylpyrrolidin-2-yl)methyl]-1H-indole;
(R)-5-Tert-butyl-3-[(N-methylpyrrolidin-2-yl)methyl]-1H-indole;
(R)-5-Isopropyl-3-[(N-methylpyrrolidin-2-yl )methyl]-1H-indole; and
5-Ethyl-3-(2-pyrrolidinylethyl)-1H-indole.

In the most preferred embodiments of the invention, the compounds of Formula I include:
5-Isopropyl-3-(2-pyrrolidinylethyl)-1H-indole;
5-Tert-butyl-3-(2-pyrrolidinylethyl)-1H-indole; and
5-Methyl-3-(2-pyrrolinylethyl )-1H-indole.

Acid addition salts of the compounds of Formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

Some of the compounds of the present invention have chiral centres, e.g. those in which one of $R^5$ and $R^6$ is hydroxy or loweralkoxy and those in which $R^2$ is a group of Formula II or III. The invention extends to cover all structural and optical isomers of the various compounds, as well as racemic mixtures thereof.

The compounds of the present invention can be prepared by processes analogous to those established in the art. Therefore, in general, compounds of Formula I can be prepared by treating an indole of Formula A (Scheme 1), wherein $R^1$ is loweralkyl, with appropriate reagents to functionalize the 3 position of the indole ring ($R^2$) with either a group of Formula II, III, IV or V. For example, to provide compounds of Formula I wherein $R^2$ is a group of Formula II, indole A can be condensed with maleimide B, wherein $R^3$ is H or loweralkyl, under acidic conditions at temperatures ranging from about 65–155° C., to provide intermediate C as shown in Scheme 1. Preferred conditions are acetic acid at temperatures of about 100–110° C. Intermediate C can then be reduced to the desired compound of Formula I using lithium aluminum hydride, lithium borohydride or diborane as reducing agent, in an inert solvent such as tetrahydrofuran, dioxane or diethyl ether at temperatures of from about 25–100° C. Preferred is the reduction with lithium aluminum hydride in tetrahydrofuran at a temperature of about 65° C.

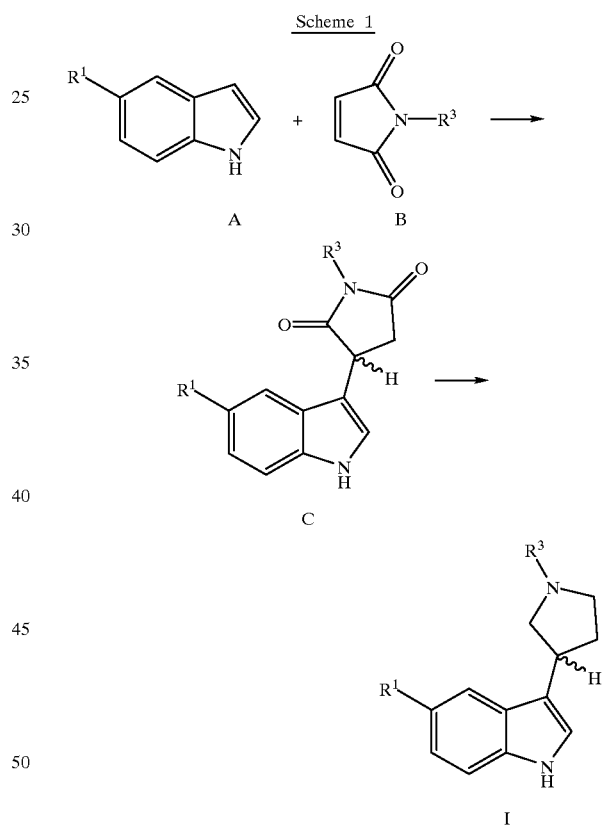

Scheme 1

Compounds of Formula I wherein $R^2$ is a group of Formula III, can be prepared as shown in Scheme 2. Reagent D, in which R is, for example, benzyl or t-butyl, can be condensed with indole A, wherein $R^1$ is as defined above, typically by first converting the indole to a magnesium derivative by reaction with a suitable Grignard reagent, such as t-butyl- or ethyl-magnesium bromide, in an inert solvent. Then the magnesium derivative so formed can be reacted in situ with a reagent of Formula D to provide intermediates of Formula E. Suitable solvents include tetrahydrofuran and diethylether (which is preferred). The reaction can be conducted at temperatures ranging from −30 to 65° C., suitably at room temperature. Intermediate E can be reduced with hydride reducing agents directly to provide compounds of Formula I wherein $R^4$ is methyl. The preferred reducing conditions are lithium aluminum hydride in tetrahydrofuran at a temperature of around 65° C. If this reduction is carried out with a smaller amount of reducing agent, compounds of Formula I, wherein one of $R^5$ and $R^6$ is hydroxyl and $R^2$ is a group of Formula II, can be isolated. This hydroxy group can then be alkylated using standard conditions (for example alkyl halide and potassium carbonate in acetonitrile) or displaced with, for example, loweralkyl lithium reagents, to provide compounds of Formula I wherein one of $R^5$ and $R^6$ is loweralkoxy or loweralkyl, respectively. Alternatively, intermediate E can be deprotected under standard conditions, for example sodium hydroxide in methanol, to provide intermediates F (compounds of Formula I where $R^4$ is hydrogen). Intermediate F can then be alkylated on the pyrrolidine nitrogen by treatment with $R^4$—X, wherein $R^4$ is loweralkyl and X is a suitable leaving group such as halogen, in the presence of a base in an inert solvent to provide intermediate G. Suitable alkylation conditions include potassium carbonate in acetonitrile or triethylamine in dichloromethane. Temperatures can be in the range of 25 to 85° C., preferably at room temperature. Intermediate G can be reduced as described above to provide compounds of Formula I, wherein $R^4$ is loweralkyl.

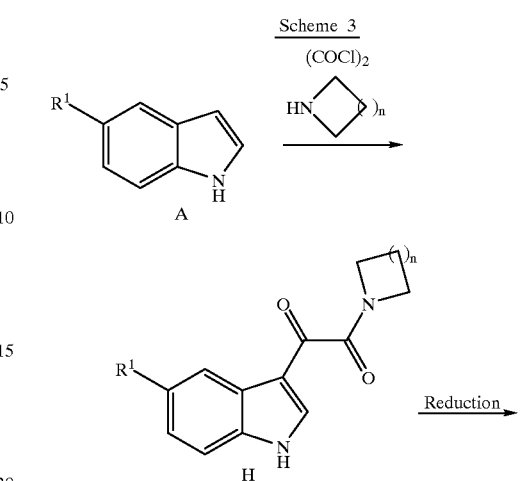

Scheme 3

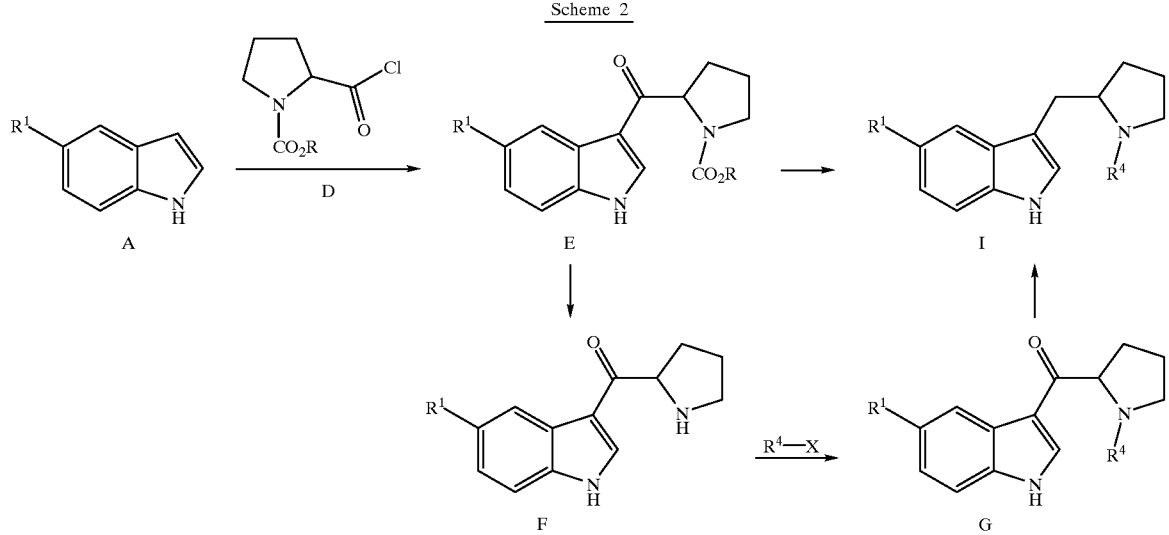

Scheme 2

To provide compounds of Formula I wherein $R^2$ is a group of Formula IV, indole A can be treated with oxalyl chloride and then the appropriate amine to provide intermediate H, followed by hydride reduction as shown in Scheme 3. The first step of these reactions can be conducted in an inert solvent such as diethyl ether (preferred) or dichloromethane, and at temperatures in the range of 0–65° C., preferably 25–65° C. The reduction can be performed as described above. If this reduction is carried out with a smaller amount of reducing agent, compounds of Formula I, wherein one of $R^5$ and $R^6$ is hydroxyl and $R^2$ is a group of Formula IV, can be isolated. This hydroxy group can then be alkylated using standard conditions (for example alkyl halide and potassium carbonate in acetonitrile) or displaced with, for example, loweralkyl lithium reagents, to provide compounds of Formula I wherein one of $R^5$ and $R^6$ is loweralkoxy or loweralkyl respectively. Compounds of Formula I where $R^2$ is a group of Formula V can be prepared as described above by substituting pyrroline as the amine.

-continued

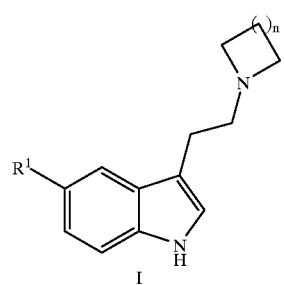

The indoles of Formula A are either commercially available or can be prepared using standard procedures. For example, as shown in Scheme 4, a 4-substituted aniline of Formula J, wherein $R^1$ is loweralkyl, can be treated with 2-bromoacetaldehyde diethylacetal in the presence of a base such as sodium bicarbonate or potassium carbonate in an alcoholic solvent at temperatures in the range of 60–100° C., to provide intermediates of Formula K. Preferred conditions are sodium bicarbonate in ethanol at around 80° C. Intermediates of Formula K can be cyclized in the presence of an acid/anhydride mixture at temperatures in the range of 60–100° C., to provide indoles of, for example, Formula L. The preferred conditions are trifluoroacetic anhydride and trifluoroacetic acid at refluxing temperatures. Finally, compounds of Formula L can be treated with base to remove the trifluoroacetate on the nitrogen to provide indoles of Formula A. Preferred conditions for this reaction are potassium hydroxide in ethanol at room temperature. The anilines of Formula J, are either commercially available or can be prepared using processes analogous to those established in the art.

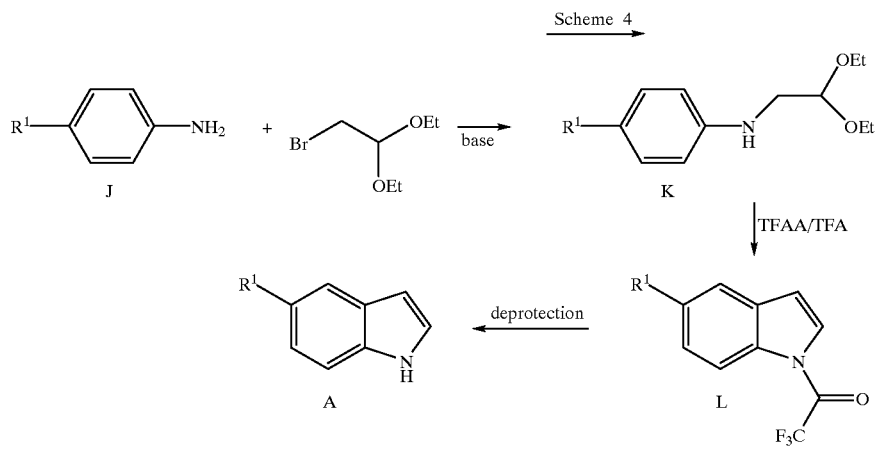

An alternative procedure for preparing compounds of Formula I wherein $R^1$ is ethyl is shown in Scheme 5. Indoles of Formulae M, N and O, wherein Y is a suitable leaving group such as halo or triflate (preferably bromo), can be coupled with a vinyl trialkylstannane of, for example, Formula P, under standard palladium-cross coupling conditions. It will be appreciated that other metal coupling reagents could be used in place of the vinyl stannane, for example, a vinyl boronic acid, chloro zinc and the like. Preferred coupling conditions include refluxing the indole and vinyl metal reagent in an inert solvent such as dimethylformamide or toluene in the presence of tetrakis(triphenylphosphine) palladium (0). Following the coupling reaction, the carbonyls can be reduced using standard hydride reducing conditions as described above and the double bond of the vinyl group, hydrogenated using catalytic amounts of palladium on carbon in an inert solvent (preferably ethyl acetate) in a hydrogen atmosphere at room temperature.

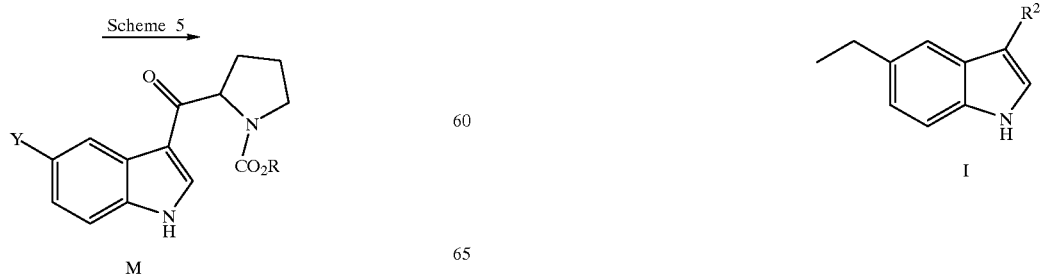

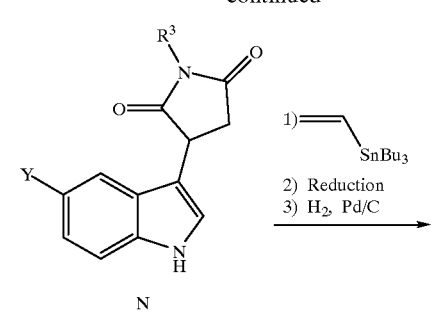

-continued

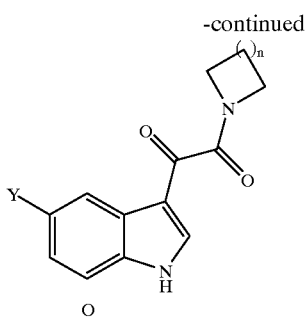

O

Intermediates of Formula M, N and O may be prepared, for example, from 5-bromoindole by applying the same procedures used for the preparation of intermediates of Formula C, E and H respectively.

In an embodiment of the invention, the compound is provided in labeled form, such as radiolabeled form, e. g. labeled by incorporation within its structure $^3$H or $^{14}$C or by conjugation to $^{125}$I. In another aspect of the invention, the compounds in labeled form can be used to identify 5-HT$^{1D}$-like receptor ligands by techniques common in the art. This can be achieved by incubating the receptor or tissue in the presence of a ligand candidate and then incubating the resulting preparation with an equimolar amount of radiolabeled compound of the invention such as [$^3$H]-5-tert-butyl-3-(2-pyrrolidinylethyl)-1H-indole. 5-HT$_{1D}$-like receptor ligands are thus revealed as those that are not significantly displaced by the radiolabeled compound of the present invention. Alternatively, 5-HT$^{1D}$-like receptor ligand candidates may be identified by first incubating a radiolabeled form of a compound of the invention then incubating the resulting preparation in the presence of the candidate ligand. A more potent 5-HT$_{1D}$-like receptor ligand will, at equimolar concentration, displace the radiolabeled compound of the invention.

The present compounds are useful as pharmaceuticals for the treatment of various conditions in which the use of a 5-HT$_{1D}$-like ligand is indicated, such as for the treatment of migraine, cluster headache and portal tension, a condition characterized by increased portal vein blood flow and typically associated with cirrhosis of the liver.

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate or hydrate thereof, in an amount effective to treat the target indication.

The compounds of the present invention may be administered by any convenient route, for example by oral, parenteral, buccal, sublingual, nasal, rectal or transdermal administration and the pharmaceutical compositions formulated accordingly.

Compounds of Formula I and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Each dosage unit for oral administration contains preferably from 1 to 250 mg (and for parenteral administration contains preferably from 1 to 25 mg) of a compound of Formula I or IV or a pharmaceutically acceptable salt thereof calculated as the free base. The pharmaceutically acceptable compounds of the invention will normally be administered in a daily dosage regimen (for an adult patient) of, for example, an oral dose of from 1 mg to 500 mg, preferably between 10 mg and 400 mg, e.g., between 10 mg and 250 mg, or an intravenous, subcutaneous or intramuscular dose of between 0.1 mg and 100 mg, preferably between 0.1 mg and 50 mg, e.g., between 1 mg and 25 mg, of a compound of Formula I or IV or a pharmaceutically acceptable salt, solvate or hydrate thereof calculated as the free base, the compound being administered 1 to 4 times per day. Suitably, the compounds will be administered for a period of continuous therapy, for example for a week or more.

EXAMPLE 1(a)

4-Isopropyl-N-(2,2-diethoxyethyl)aniline

A solution of 4-isopropylaniline (7.6 mL, 56 mmol), 2-bromoacetaldehyde diethyl acetal (5.5 mL, 36 mmol) and sodium bicarbonate (4.8 g, 57 mmol) in ethanol (60 mL) was stirred at reflux for 3 days under argon. After cooling to room temperature, the ethanol was removed in vacuo and the product was partitioned between ether and water, washed sequentially with water and brine, and dried over sodium sulfate. After removal of the solvent in vacuo, flash chromatography (silica, 10% ethyl acetate in hexanes) yielded 4-isopropyl-N-(2,2-diethoxyethyl) aniline (8.23 g, 90%).

In a like manner, the following compound was prepared:
(b) 4-Tert-butyl-N-(2,2-diethoxyethyl)aniline; from 4-tert-butylaniline (70%).
(c) 4-Sec-butyl-N-(2,2-diethoxyethyl)aniline; from 4-sec-butylaniline (56%).

EXAMPLE 2(a)

5-Isopropyl-1-trifluoroacetylindole

A solution of 4-isopropyl-N-(2,2-diethoxyethyl)aniline (Example 1a, 2.62 g, 10.4 mmol) and trifluoroacetic anhydride (20 mL, 14 mmol) in trifluoroacetic acid (20 mL, 26 mmol) was stirred at 0° C. for 10 minutes before warming to reflux and adding a second portion of trifluoroacetic acid (15 mL, 20 mmol). The resulting mixture was stirred at reflux for 3 days prior to removal of the volatiles in vacuo. Flash chromatography (silica, 5% ethyl acetate in hexane) yielded 5-isopropyl-1-trifluoroacetylindole (728 mg, 27%).

In a like manner, the following compound was prepared:
(b) 5-Tert-butyl-1-trifluoroacetylindole; from 4-tert-butyl-N-(2,2-diethoxyethyl) aniline (Example 1b) (23%).
(c) 5-Sec-butyl-1-trifluoroacetylindole; from 4-sec-butyl-N-(2,2-diethoxyethyl) aniline (Example 1c) (18%).

EXAMPLE 3(a)

5-Isopropyl-1H-indole

A solution of potassium hydroxide in methanol (5% w/v, 17 mL) containing 5-isopropyl-1-trifluoroacetylindole (Example 2a, 1.163 g, 4.55 mmol) was stirred at room temperature overnight. After removal of the methanol, the product was partitioned between ethyl acetate and water, washed sequentially with water and brine, and dried over sodium sulfate. Flash chromatography (silica, 10% ethyl acetate in hexanes) yielded 5-isopropyl-1H-indole (715 mg, 98%).

In a like manner, the following compound was prepared:
(b) 5-Tert-butyl-1H-indole; from 5-tert-butyl-1-trifluoroacetylindole (Example 2b) (95%).
(c) 5-Sec-butyl-1H-indole; from 5-sec-butyl-1-trifluoroacetylindole (Example 2c) (94%).

EXAMPLE 4(a)

5-Isopropyl-3-[(N-pyrrolidinyl)glyoxyl]-1H-indole

A solution of oxalyl chloride in dichloromethane (2.23 mL, 2M, 4.46 mmol) was added in a dropwise manner to a solution of 5-isopropyl-1H-indole (Example 3a, 711 mg, 4.46 mmol) in ether (15 mL) at 0° C. under argon. The resulting solution was stirred at a gentle reflux for 22 h. After cooling to 0° C., a solution of pyrrolidine (0.80 mL, 9.6 mmol) and triethylamine (1.30 mL, 9.4 mmol) in THF (10 mL) was added and the resulting solution was stirred at 0° C. for 1.5 h. The reaction mixture was partitioned between dichloromethane and water, and the aqueous layer was extracted with dichloromethane (2x). The combined organic layers were washed with brine and dried over sodium sulfate. After removal of the solvent in vacuo, flash chromatography (silica, 70–100% ethyl acetate in hexanes) yielded 5-isopropyl-3-[(N-pyrrolidinyl)glyoxyl]-1H-indole (1.27 g, 100%).

In a like manner, the following compounds were prepared:
(b) 5-Tert-butyl-3-[(N-pyrrolidinyl)glyoxyl]-1H-indole; from 5-tert-butyl-1H-indole (Example 3b) (17%).
(c) 5-Methyl-3-[(N-pyrrolidinyl)glyoxyl]-1H-indole: from 5-methyl-1H-indole (83%).
(d) 5-Methyl-3-[(N-pyrrolinyl)glyoxyl]-1H-indole; from 5-methyl-1H-indole and pyrroline (65%).
(e) 5-Sec-butyl-3-[(N-pyrrolidinyl)glyoxyl]-1H-indole; from 5-sec-butyl-1H-indole (Example 3c) (33%).
(f) 5-Sec-butyl-3-[(N-pyrrolinyl)glyoxyl]-1H-indole; from 5-sec-butyl-1H-indole (Example 3c) and pyrroline (32%).

EXAMPLE 5(a)

(R)-3-[(N-Benzyloxycarbonylpyrrolidin-2-yl)carbonyl]-5-bromo-1H-indole

To a stirred solution of N-benzyloxycarbonyl-R-proline (2.5 g, 10.0 mmol) in anhydrous methylene chloride was added a solution of oxalyl chloride (2M solution in methylene chloride, 7 mL, 15.0 mmol). The resulting mixture was stirred at room temperature under argon for 2 hours. The solvent and excess oxalyl chloride were evaporated under reduced pressure and the crude product washed with hexane (3×10 mL) and evaporated to dryness to provide N-benzyloxycarbonyl-R-proline acid chloride which was used directly for the next reaction. N-Benzyloxycarbonyl-R-proline acid chloride from the above reaction was dissolved in anhydrous diethyl ether (30 mL) and added at 0° C. to a solution of 5-bromoindole (2.9 g, 15.0 mmol) and t-butylmagnesium chloride (2M solution in diethyl ether, 8.3 mL, 16.5 mmol) in anhydrous diethyl ether (30 mL). The resulting mixture was stirred at room temperature under argon for 45 minutes and then ethyl acetate (150 mL) and saturated sodium bicarbonate (30 mL) were added. The organic layer was dried and evaporated under reduced pressure to provide a yellow oil. The title compound was crystallized using hexane/ethyl acetate (9:1) to provide a white solid (3.07 g, 72%). mp 95–96° C.

In a like manner, the following additional compounds were prepared:
(b) (R)-3-[(N-Benzyloxycarbonylpyrrolidin-2-yl)carbonyl]-5-methyl-1H-indole: from 5-methyl-1H-indole.
(c) (R)-3-[(N-Benzyloxycarbonylpyrrolidin-2-yl)carbonyl]-5-tert-butyl-1H-indole: from 5-tert-butyl-1H-indole (Example 3b) (71%; white solid; mp 220–224° C.).
(d) (R)-3-[(N-Benzyloxycarbonylpyrrolidin-2-yl)carbonyl]-5-isopropyl-1H-indole: from 5-isopropyl-1H-indole (Example 3a) (61%; white foam).
(e) (S)-3-[(N-Benzyloxycarbonylpyrrolidin-2-yl)carbonyl]-5-methyl-1H-indole: from N-benzyloxycarbonyl-S-proline and 5-methyl-1H-indole.

EXAMPLE 6

(R)-5-Methyl-3-[(pyrrolidin-2-yl)carbonyl]-1H-indole

To a stirred solution of (R)-3-[(N-benzyloxycarbonylpyrrolidin-2-yl)carbonyl)]-5-methyl-1H-indole (Example 5b) in EtOAc (10 mL) was added EtOH (10 mL) and Pd/C (1.3 g). The reaction mixture was stirred at room temperature under a hydrogen atmosphere until the starting material was consumed. At this time, the reaction mixture was filtered through celite and the solvent was evaporated. The crude product was purified by column chromatography (4:1 $CHCl_3$: $NH_3$ (2M in MeOH) to yield the title compound (121.5 mg, 15%) as a white solid (mp 194–196° C.).

EXAMPLE 7(a)

3-(5-Bromo-1H-indol-3-yl)-N-methylsuccinimide

To a solution of 5-bromoindole (5 g, 25.5 mmol) in glacial acetic acid (60 mL) was added N-methylmaleimide (6.1 g, 56.11 mmol) and the resulting mixture was heated to reflux for 4 days. The acetic acid was removed by distillation and the crude product was dissolved in diethyl ether (500 mL) and washed with saturated sodium bicarbonate (2×100 mL) and brine (3×100 mL). The solvent was evaporated and the residue chromatographed on silica gel using hexane/ethyl acetate (1:1) as the eluent to provide 3-(5-bromo-1H-indol-3-yl)-N-methylsuccinimide (5.85 g, 75%). Yellow solid, mp 194–195° C.

In a like manner, the following additional compound was prepared:

(b) 3-(5-Methyl-1H-indol-3-yl)-N-methylsuccinimide: from 5-methyl-1H-indole (56%; yellow solid).

EXAMPLE 8(a)

5-Isopropyl-3-(2-pyrrolidinylethyl)-1H-indole

LAH (20 mL, 1M in THF, 20 mmol) was added to a solution of 5-isopropyl-3-[(N-pyrrolidinyl)glyoxyl]-1H-indole (Example 4a, 698.9 mg, 2.45 mmol) in THF (26 mL) at 0° C. The resulting solution was refluxed gently for 2.5 h prior to quenching with sodium sulfate decahydrate. The product was taken into ethyl acetate, filtered to remove the solid residue, and the solvent was removed in vacuo. Flash chromatography (silica gel, 6% 2M methanolic ammonia in dichloromethane) yielded 5-isopropyl-3-(2-pyrrolidinylethyl)-1H-indole (358.5 mg, 57%; mp 70–72° C.; elemental analysis calculated for $C_{17}H_{24}N_2$: %C 79.64, %H 9.44, %N 10.93; found %C 79.85, %H 9.35, %N 11.02). **A second fraction of insufficient purity was also isolated (ca. 225 mg, 36%).

In a like manner, the following compounds were prepared:

(b) 5-Tert-butyl-3-(2-pyrrolidinylethyl)-1H-indole: from 5-tert-butyl-3-[(N-pyrrolidinyl) glyoxyl]-1H-indole (Example 4b) (90%; mp 112–115° C.; elemental analysis calculated for $C_{18}H_{26}N_2$: %C 79.96, %H 9.69, %N 10.36; found %C 80.00, %H 9.14, %N 10.32).

(c) 5-Methyl-3-(2-pyrrolidinylethyl)-1H-indole: from 5-methyl-3-[(N-pyrrolidinyl) glyoxyl]-1H-indole (Example 4c) (64%; mp 66–68° C.).

(d) 5-Methyl-3-(2-pyrrolinylethyl)-1H-indole: from 5-methyl-3-[(N-pyrrolidinyl) glyoxyl]-1H-indole (Example 4d) (39%; mp 106–108° C.; HRMS-FAB+ for $C_{15}H_{18}N_2$: calculated $MH^+$:227.1548; found $MH^+$:227.1541).

(e) (R)-3-[(N-Methylpyrrolidin-2-yl)methyl]-5-methyl-1H-indole: from (R)-3-[(N-Benzyloxycarbonylpyrrolidin-2-yl)carbonyl]-5-methyl-1H-indole (Example 5b) (52%; yellow oil; HRMS-FAB+ for $C_{15}H_{20}N_2$: calculated $MH^+$:229.1705; found $MH^+$:229. 1706).

(f) (R)-3-[(N-Methylpyrrolidin-2-yl)methyl]-5-tert-butyl-1H-indole: from (R)-3-[(N-Benzyloxycarbonylpyrrolidin-2-yl)carbonyl]-5-tert-butyl-1H-indole (Example 5c) (57%; yellow foam; HRMS-FAB+ for $C_{17}H_{26}N_2$: calculated $MH^+$:271.2174; found $MH^+$:271.2160).

(g) (R)-3-[(N-Methylpyrrolidin-2-yl)methyl]-5-isopropyl-1H-indole: from (R)-3-[(N-Benzyloxycarbonylpyrrolidin-2-yl)carbonyl]-5-isopropyl-1H-indole (Example 5d) (91%; white solid; mp 60–62° C.; HRMS-FAB+ for $C_{17}H_{24}N_2$: calculated $MH^+$:257.2018; found $MH^+$:257.2009).

(h) (S)-3-[(N-Methylpyrrolidin-2-yl)methyl]-5-methyl-1H-indole: from (S)-3-[(N-Benzyloxycarbonylpyrrolidin-2-yl)carbonyl]-5-methyl-1H-indole (Example 5e) (HRMS-FAB+ for $C_{15}H_{20}N_2$: calculated $MH^+$:229.1705; found $MH^+$:229.1693).

(i) 5-Methyl-3-(N-methylpyrrolidin-3-yl)-1H-indole: from 3-(5-Methyl-1H-indol-3-yl)-N-methylsuccinimide (Example 7b) (70%; mp 102–104 ° C.; HRMS-FAB+for $C_{14}H_{18}N_2$: calculated $MH^+$:215.1548; found $MH^+$:215.1539).

(j) (R)-5-Methyl-3-[(pyrrolidin-2-yl)methyl]-1H-indole: from (R)-5-Methyl-3-[(pyrrolidin-2-yl)carbonyl]-1H-indole (Example 6) (44%; yellow powder; mp 88–90° C.; HRMS-FAB+for $C_{14}H_{18}N_2$: calculated $MH^+$:215.1548; found $MH^+$:215.1550).

(k) 5-Sec-butyl-3-(2-pyrrolidinylethyl)-1H-indole: from 5-sec-butyl-3-[(N-pyrrolidinyl)glyoxyl]-1H-indole (Example 4e) (59%; pale yellow solid; mp 58–62° C.).

(l) 5-Sec-butyl-3-(2-pyrrolinylethyl)-1H-indole: from 5-sec-butyl-3-[(N-pyrrolinyl)glyoxyl]-1H-indole (Example 4f) (31%; white solid; mp 118–120° C.).

EXAMPLE 9

5-Bromo-3-(2-pyrrolidinylethyl)-1H-indole

To a solution of 5-bromoindole (3.92 g, 20 mmol) in ether (50 mL), cooled to 0° C. was added a solution of oxalyl chloride in dichloromethane (2M, 10 mL) dropwise. The resulting mixture was stirred at room temperature overnight and then cooled to 0° C. and pyrrolidine (6.7 mL, 80 mmol) was added dropwise. After stirring for 2 hours at room temperature, the mixture was poured into water (50 mL) and extracted with dichloromethane (3×100 mL). The combined organic phases were dried over sodium sulfate and evaporated to a white amorphous solid which was washed with ethyl acetate (50 mL) to give 5-bromo-3-[(N-pyrrolidinyl)glyoxyl]-1H-indole (2.87 g, 45%). mp 212–213° C.; $^1H$ NMR ($CDCl_3$, 300 MHz) d: 10.69 (s, 1H), 8.49 (d, J=1.5 Hz, 1H), 7.87 (d, J=3.0 Hz, 1H), 7.31 (dd, J=8.6, 1.5 Hz, 1H), 7.17 (d, J=8.6 Hz, 1H), 3.59 (m, 4H), 1.94 (m, 4H).

A solution of LAH (36 mL, 1M in THF, 36 mmol) was added slowly to a cooled (0° C.) solution of 5-bromo-3-[(N-pyrrolidinyl)glyoxyl]-1H-indole (2.87 g, 8.9 mmol) in THF (100 mL). Once the addition was completed, the reaction mixture was stirred at reflux overnight prior to quenching with sodium sulfate decahydrate. The product was taken into ethyl acetate, filtered to remove the solid residue, and the solvent was removed in vacuo to yield the title compound (2.08 g, 72%).

EXAMPLE 10(a)

(R)-5-Vinyl-3-[(N-methylpyrrolidin-2-yl)methyl]-1H-indole

A solution (R)-3-(N-Benzyloxycarbonylpyrrolidin-2-ylcarbonyl)-5-bromo-1H-indole (Example 5a, 252 mg, 0.59 mmol), tributyl(vinyl)tin (0.20 mL, 0.68 mmol) and tetrakistriphenyphosphine palladium (0) (84 mg, 0.073 mmol) in anhydrous DMF (3 mL) was stirred at 95–100° C. for 1 day. After cooling to room temperature, the product was taken into ethyl acetate, filtered through celite, washed with water (2×) and brine (1×), dried over sodium sulfate and the solvent was removed in vacuo. Flash chromatography on silica gel (60–100% ethyl acetate in hexanes) yielded (R)-5-vinyl-3-[(N-carbobenzyloxypyrrolidin-2-yl)carbonyl]-1H-indole (115 mg, 52%). A solution of LAH (0.77 mL, 1M in THF, 0.77 mmol) was added slowly to a cooled (0° C.) solution of (R)-5-vinyl-3-[(N-carbobenzyloxypyrrolidin-2-yl) carbonyl]-1H-indole (115 mg, 0.31 mmol) in THF (5 mL). Once the addition was completed, the reaction mixture was stirred at reflux for 2 h prior to quenching with sodium sulfate decahydrate. The product was taken into ethyl acetate, filtered to remove the solid residue, and the solvent was removed in vacuo. Flash chromatography on silica gel (5% 2M methanolic ammonia in dichloromethane) yielded (R)-5-vinyl-3-[(N-methylpyrrolidin-2-yl) methyl]-1H-indole (52 mg, 71%). HRMS-FAB$^+$ for $C_{16}H_{20}N_2$: calculated MH$^+$:241.17047; found MH$^+$:241.17036.

In a like manner, the following compounds were prepared:

(b) 5-Vinyl-3-(N-methylpyrrolidin-3-yl)-1H-indole: from 3-(5-bromo-1H-indol-3-yl -N-methylsuccinimide (Example 7a) (27% over 2 steps, HRMS-FAB$^+$ for $C_{15}H_{18}N_2$: calculated MH$^+$:227.15483; found MH$^+$:227.15356).

(c) 5-Vinyl-3-(2-pyrrolidinylethyl)-1H-indole: from 5-bromo-3-(2-pyrrolidinylethyl) -1H-indole (Example 9) (7%, larger scale no purification of intermediate).

EXAMPLE 11(a)

5-Ethyl-3-(2-pyrrolidinylethyl)-1H-indole

5-Vinyl-3-(2-pyrrolidinylethyl)-1H-indole (Example 10c, 8.0 mg, 0.033 mmol) in ethyl acetate (3 mL) containing a spatula tip of Pd/C (10%) was stirred at room temperature under an atmosphere of hydrogen for 2.5 h. Filtration through celite using 10% 2M methanolic ammonia in dichloromethane and evaporation of the solvent in vacuo. A final filtration through silica gel using 10% 2M methanolic ammonia in dichloromethane yielded 5-ethyl-3-(2-pyrrolidinylethyl) -1H-indole (4.5 mg, 56%).

In a like manner the following compounds were prepared:

(b) (R)-5-Ethyl-3-[(N-methylpyrrolidin-2-yl)methyl]-1 H-indole; from (R)-5-vinyl-3-[(N-methylpyrrolidin-2-yl) methyl]-1H-indole (Example 10a) (82%, HRMS-FAB$^+$ for $C_{16}H_{22}N_2$: calculated MH$^+$:243.18663; found MH$^+$:243.18712).

(c) 5-Ethyl-3-(N-methylpyrrolidin-3-yl)-1H-indole; from 5-vinyl-3-[N-methylpyrrolidin-3-yl]-1H-indole (Example 10b) (99%, HRMS-FAB$^+$ for $C_{15}H_{20}N_2$: calculated MH$^+$:229.17097; found MH$^+$:229.17201).

| Summary of Exemplified Compounds of Formula I | | |
|---|---|---|
| Example # | R$^1$ | R$^2$ |
| 8a | isopropyl | |
| 8b | tert-butyl | |
| 8c | methyl | |
| 8d | methyl | |
| 8e | methyl | |
| 8f | tert-butyl | |
| 8g | isopropyl | |
| 8h | methyl | |
| 8i | methyl | |
| 8j | methyl | |

-continued

Summary of Exemplified Compounds of Formula I

| Example # | R¹ | R² |
|---|---|---|
| 8k | sec-butyl | 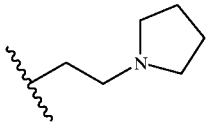 |
| 8l | sec-butyl | 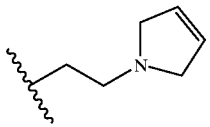 |
| 11a | ethyl | 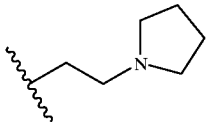 |
| 11b | ethyl | 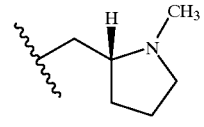 |
| 11c | ethyl | 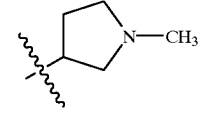 |

EXAMPLE 12

Agonist Assay

The in vitro evaluation of the 5-$HT_{1D}$-like receptor agonist activity of compounds of the invention was carried out by testing the extent to which they mimic sumatriptan, the marketed antimigraine drug, in contracting the rabbit saphenous vein (Perez, M. et al. J. Med. Chem. 1995, 38:3602–3607).

Tissues were obtained from male New Zealand White rabbits (~3–4 kg) which were sacrificed by an overdose of pentobarbital. The saphenous veins from both the left and right side were cleaned of fat and connective tissue and placed in Krebs solution (118 mM NaCl, 11 mM glucose, 25 mM $NaHCO_3$, 4.7 mM KCl, 2.5 mM $CaCl_2.2H_2O$, 1.2 mM $KH_2PO_4$, and 1.2 mM $MgSO_4.7H_2O$. Ring segments of the vein (4–5 mm in length) were cut and the endothelium gently removed. The segments were mounted in 10 mL baths containing Krebs buffer and were constantly aerated with 95% oxygen/5% carbon dioxide and maintained at 37° C. and pH 7.4 in order to record the isometric tension. A resting tension of 2.5 g was applied and the tissues allowed to equilibrate for 90 minutes, with washing every 15–20 minutes. After the equilibrium period, the rings were depolarized by the addition of two aliquots of KCl (80 mM final concentration) separated by a 20 minute washing period. The tissues were then exposed to prazosin, idazoxan and indomethacin (all 1 µM final concentration) for 30 minutes in order to exclude the actions of $\alpha_1$- and $\alpha_2$-adrenergic receptors and prostaglandin receptors respectively. Cumulative concentration-effect curves were then constructed for sumatriptan and the test compounds. Responses were calculated as a percentage of the maximal contraction evoked by 80 mM KCl. Only one compound was tested per preparation.

The following Table illustrates the in vitro activities for the compounds of the invention on the rabbit isolated saphenous vein. $EC_{50}$ represents the concentration of the compound which causes 50% of the maximum contraction effected by it.

| Example # | $EC_{50}$ (µM) |
|---|---|
| sumatriptan | 0.22 |
| 7e | 0.10 |
| 7f | 0.052 |
| 7g | 0.029 |
| 7h | 1.8 |
| 7i | 0.47 |
| 7j | 0.83 |
| 8a | 0.25 |
| 8b | 1.2 |
| 8c | 0.59 |
| 8d | 2.9 |
| 11b | 0.015 |
| 11c | 0.90 |

EXAMPLE 13

Inhibition of Protein Extravasation

Compounds of the inventions were evaluated for their ability to block neurogenic inflammation via inhibition of protein extravasation using the trigeminal stimulation assay as described in Markowitz, et al. J, Neurosci. 1987, 7:4129 and Lee, et al. Brain Res, 1993, 626:303. This is believed to indicate a compound's ability to act as an agonist at the 5-$HT_{1D\alpha}$and/or 5-$HT_{1F}$ receptors.

Guinea pigs were anesthetized with pentobarbitone sodium (60 mg kg⁻¹, i.p.). Animals were placed in a stereotaxic frame (DKI 900, David Kopf Instruments, Tujunga, Calif., U.S.A.). The right femoral vein was exposed and [$^{125}$I]-BSA (50 µCi kg⁻¹) was injected as a bolus. With the incisor bar set at −1.5 mm from the horizontal line, the calvarium was exposed by a midline incision. Symmetrical burr holes (2 mm in diameter) were drilled at 3.7 mm posterior to the bregma and 3.2 mm lateral to the sagittal suture. Bipolar electrodes (50 mm shaft, Rhodes Medical Instruments, Woodland Hills, Calif., U.S.A.) were lowered into the trigeminal ganglia to a depth of 9.5 mm from the dura mater overlying the dorsal surface of the brain. The right trigeminal ganglion was stimulated for 5 min (0.6 mA, 5 ms, 5 Hz) (Pulsemaster A300 and Stimulus Isolator A365, World Precision Instruments, San Carlos, Calif., U.S.A.; Oscilloscope V-134, Hitachi Densi, Tokyo, Japan). In order to remove iodinated albumin completely from the lumen of blood vessels, animals were perfused via the left cardiac ventricle for 2 min with saline at a constant pressure of 100 mm Hg. After opening the skull, the brain was removed. The dura mater was rinsed and dissected bilaterally. Radioactivity was determined on two sides with a gamma counter (Micromedic 4/600, Micromedic Systems, Inc., Huntsville, Ala., U.S.A.) as previously described (Markowitz, et al., 1987 and Lee, et al., 1993).

Results from this assay, expressed as an $IC_{50}$ (nM/kg of drug), are shown in the table below for the reference compound, sumatriptan, and select compounds of the invention.

| Example # | IC$_{50}$ (nM/kg) |
|---|---|
| sumatriptan | 3.3–7 |
| 8a | 0.73 |
| 8b | 6.7 |
| 8c | 2.7 |

We claim:

1. A compound according to Formula I:

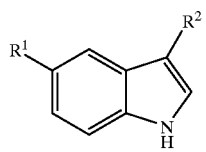

wherein:

$R^1$ is a linear or branched lower alkyl;
$R^2$ is a group of Formula IV:

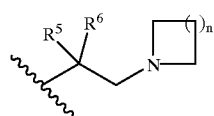

n is 2;

or a salt or hydrate thereof.

2. A pharmaceutical composition, comprising a pharmaceutically acceptable carrier and, in an amount effective to stimulate a 5-$HT_{1D}$- like receptor, a compound of Formula I as recited in claim 1.

3. A compound according to claim 1, wherein $R^1$ is $C_1$–$C_4$ alkyl, or a salt or hydrate thereof.

4. A compound according to claim 3, which is selected from:

5-methyl-3-(2-pyrrolidinylethyl)-1H-indole;
5-ethyl-3-(2-pyrrolidinylethyl)-1H-indole;
5-isopropyl-3-(2-pyrrolidinylethyl)-1H-indole; and
5-tert-butyl-3-(2-pyrrolidinylethyl)-1H-indole;
or a salt or hydrate thereof.

5. A compound according to claim 4, which is 5-tert-butyl-3-(2-pyrrolidinylethyl )-1H-indole,
or a salt or hydrate thereof.

6. A pharmaceutical composition according to claim 2, wherein said compound of Formula I is selected from:

5-methyl-3-(2-pyrrolidinylethyl)-1H-indole;
5-ethyl-3-(2-pyrrolidinylethyl)-1H-indole;
5-isopropyl-3-(2-pyrrolidinylethyl)-1H-indole; and
5-tert-butyl-3-(2-pyrrolidinylethyl)-1H-indole.

7. A pharmaceutical composition according to claim 6, wherein said compound of Formula I is:

5-tert-butyl-3-(2-pyrrolidinylethyl)-1H-indole.

* * * * *